(12) United States Patent
Ljungquist

(10) Patent No.: US 6,331,173 B1
(45) Date of Patent: *Dec. 18, 2001

(54) DEVICE FOR DISPLACING A MEMBER IN A CONTAINER

(75) Inventor: Olle Ljungquist, Täby (SE)

(73) Assignee: Pharmacia AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/294,552

(22) Filed: Apr. 20, 1999

(51) Int. Cl.[7] ........................................... A61M 5/00
(52) U.S. Cl. ..................... 604/191; 604/218; 604/187; 604/90; 604/82; 604/232
(58) Field of Search ..................... 604/233, 234, 604/235, 241, 242–243, 85, 87, 89, 90, 91, 82, 224, 231, 232, 83, 84, 92, 181, 187, 191, 219–221, 416, 218; 206/219–221

(56) References Cited

U.S. PATENT DOCUMENTS

| | | |
|---|---|---|
| 2,778,359 | * 1/1957 | Friedman ........................... 604/211 |
| 4,874,381 | 10/1989 | Vetter . |
| 4,968,299 | 11/1990 | Ahlstrand et al. . |
| 5,080,649 | 1/1992 | Vetter . |
| 5,454,793 | 10/1995 | Levander et al. . |
| 5,728,075 | 3/1998 | Levander . |
| 5,817,056 | 10/1998 | Tanaka et al. . |
| 5,823,998 | 10/1998 | Yamagata . |
| 5,830,193 | 11/1998 | Higashikawa . |
| 5,925,019 | * 7/1999 | Ljungquist ........................... 604/191 |

FOREIGN PATENT DOCUMENTS

WO 9314799    8/1993   (WO) .

* cited by examiner

Primary Examiner—Manuel Mendez
(74) Attorney, Agent, or Firm—Dinsmore & Shohl LLP

(57) ABSTRACT

A multi-chamber ampoule comprises a container having at least one movable partition therein, the movable partition being adapted to sealingly isolate at least two substances to be mixed with each other, a seal or plunger movably disposed in the container, a holder connected to the container, and a screw actuator engageable with the seal or plunger for displacing the same in the container. The screw actuator has a male thread, and the holder includes a female thread engageable with the screw actuator male thread. The screw actuator is provided with a bore therethrough for slidably receiving a dispensing rod.

10 Claims, 2 Drawing Sheets

DEVICE FOR DISPLACING A MEMBER IN A CONTAINER

FIELD OF THE INVENTION

The invention relates to a device for displacing a member, e. g. a plunger in a container, especially a medical multi-chamber ampoule, said plunger being slidable along an inner wall of said container in sealing contact therewith.

BACKGROUND OF THE INVENTION

Such multi chamber ampoules are previously used for storing one or more sensitive medical components, which are to be dissolved in a liquid to form an injectable solution. The solution can not be stored for a longer period of time without becoming deteriorated. However, sensitive medical components of this kind can in most cases be stored for longer periods of time, if they are isolated from the solvent or other substance, which adversely would affect the component. Very often those medical components are present in the ampoule in a freeze-dried state and stored therein in a front chamber provided in said ampoule, which chamber has an outlet opening, which usually is sealed by a membrane, or other seal, which could be removed, ruptured or penetrated by a hollow needle, such as a cannula or the like for taking out the solution. The rear of the front chamber is limited by an axially movable partition, sealingly engaging the inner wall of the ampoule and being located to prevent flow between the rear and the front chambers through an interior or exterior by-pass connection provided in the ampoule. Said partition forms the forward end of a rear chamber, in which the solvent to be added to the sensitive medical component in the front chamber is contained.

By forwardly displacing the partition a communication between the front and the rear chambers will be established through said by-pass connection. The rear end of the rear chamber is sealed by movable seal or plunger.

When the liquid in the rear chamber is to be added to the medical component in the front chamber, the rear seal or the plunger is depressed, which via the incompressible liquid, in turn will move the partition in the same direction. As soon as the partition has been moved so long, that a communication has been established between the two chambers through said by-pass connection, liquid will flow from the rear chamber into the front chamber upon further depression of the plunger.

A very well known problem in the art, is that freeze-dried medical components usually are very sensitive to mechanical influences and will deteriorate if the mechanical stresses become too strong. Thus, during the liquid addition step they require a balanced and smooth flow. In order to solve this problem a lot of devices have been proposed for providing a displacing mechanism, by means of which the plunger or the rear seal of the container can be moved in a controlled manner for obtaining the desired flow into the front chamber. In most cases devices of this kind typically comprise a means for receiving and holding an ampoule and a screw actuator, having a male thread, which cooperates with a corresponding female thread relied with the holding means of said ampoule. The pitch of the threads is low, so that each revolution of the screw actuator results in a very limited axial displacement of the actuator. Thus, in this manner, the plunger will have a smooth axial movement. Such devices have a satisfying performance for obtaining a smooth flow of liquid into the front chamber. However, this kind of prior devices presents a disadvantage in that the screw actuator has to be rotated in the backward direction to the same extent as in the forward direction for returning it to its initial position for the reception of a fresh ampoule. This is a time consuming task with no other purpose than to reset the actuator.

Therefore, there has been a need for a device, by means of which the plunger or the rear seal may be displaced in the forward direction in a smooth and uniform manner to provide a smooth flow, but which permits a quick return of the screw actuator to its initial position.

An example of such a device is disclosed in the PCT-application WO 93/14799, which presents a solution to the aforementioned problem. This prior device includes a screw actuator, having a male thread, cooperating with a female thread for the forward movement of the actuator, which for the reset readily can be brought out of its engagement with the female thread and rapidly be reset to its starting position for the reception of a new ampoule.

The prior device comprises a slotted holder, which include a female thread engagable with a screw actuator, when the longitudinal axes of the holder and of the actuator coincide. The actuator may be tilted about an axis perpendicular to its longitudinal axis and be swung out of the slot of the holder. As a result of this tilting movement, the male and female threads loose their mutual engagement, so that the actuator readily and rapidly may be brought back to its starting position, whereupon the device may be reused after the removal of the emptied ampoule.

Even if this device constitutes a progress in relation to prior solutions as regards quickness in the resetting of the device for reuse, it presents a certain number of drawbacks:
- it requires a great number of manipulations for the resetting,
- it is rather bulky,
- it can only be used for one single determined length of ampoule, and
- the manufacture thereof is rather complicated and expensive and great care must be taken when producing some of the constructional features of the instrument, in particular the producing of the female read in relation to the slot, is delicate.

SUMMARY OF THE INVENTION

The object of the invention is to provide a quickly resettable device of the above kind, which permits a smooth flow of the liquid to be added to the sensitive medical component in the front chamber, has a simple and non-expensive construction, is easy to handle and which readily and quickly may be connected to a container of optional length, having a plunger, which is to be displaced by means of the device.

By dividing the female thread into at least two parts, which by means of an actuation means may be brought into or out of an engagement position, the screw actuator may be released from its engagement with a female thread in any position along its path in the device and quickly returned to its initial position.

Preferably, said actuating means is automatically actuated, when the holder means is connected to said container. In this way the device automatically will be ready for use in a single step, without the need of any further measures for bringing the female thread parts together. Likewise, the screw actuator may easily be disconnected from the female thread in one single step by simply releasing the device from the ampoule or container.

The device may include a bayonet-like coupling for releasably holding the container or the ampoule. In this way the device readily may be connected to the container by a simple rotational movement.

BRIEF DESCRIPTION OF THE DRAWINGS

A preferred embodiment of the invention will now be described by way of example, with reference to the annexed drawing, wherein.

DETAILED DESCRIPTION OF THE INVENTION

Figure 1:
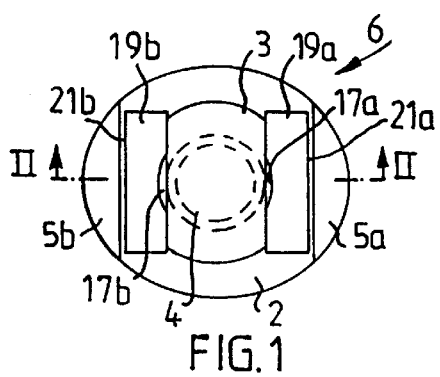
FIG. 1 is a top view of the device of the invention in an open non-assembled position.
Figure 2:
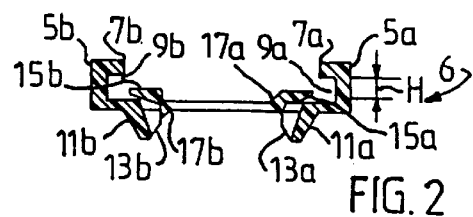
FIG. 2 is a sectional view of the open device shown in FIG. 1 along the line II—II.
Figure 3:
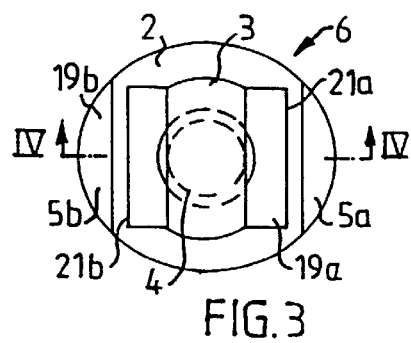
FIG. 3 is a top view corresponding to that of FIG. 1 of the device in a closed and assembled position.

The preferred embodiment of the device 1 of the invention comprises two main components, a screw actuator 4 and a holder means 6. The constructional design of the holder means 6 is illustrated in FIGS. 1–4. The holder means 6 has a substantially elliptic, in essential flat support plate 2, which best could be seen in FIGS. 1 and 3, but the shape of the plate 2 is not critical, it can have any appropriate form. The center area of the plate 2 has an opening 3, which is sized so that the screw actuator 4 of the device can be introduced therethrough. In FIGS. 1 and 3, the screw actuator 4 is indicated with broken lines but for the sake of simplicity it is not shown in the sectional views of FIGS. 2 and 4. At each longitudinal end of the support plate 2 a flange 5a, 5b is provided, which protrudes perpendicularly to the plate 2. Each flange 5a, 5b has integral therewith an inwardly directed rim 7a, 7b, the inner face of which is substantially parallel to the upper face of the support plate 2. The support plate 2 and the flanges 5a, 5b, including the rims 7a, 7b, thus form two parallel flutes 9a, 9b, the height H of which being substantially the same as the thickness of a rim 25 provided on a container 23, to which the device 1 is to be attached to. The distance D between the bottom walls of the flutes 9a, 9b is substantially the same as the greatest width of the rim 25 of said container 23.

Originating from the opposite face of the support plate 2 at the opening 3, two obliquely directed flanges 11a, 11b are provided, which are symmetrically disposed in relation to the center point of the plate 2. The end point of each oblique flange 11a, 11b carries an elastic spring 13a, 13b directed upwardly towards the opening 3. As can be seen in the cross section of FIG. 2 each spring 13a, 13b is slightly curved and forms generally a V with its corresponding oblique flange 11a, 11b. The other end of the spring 13a, 13b carries an actuating means 15a, 15b and a corresponding part of a female thread 17a, 17b. The actuating means 15a, 15 and a part of the female thread 17a, 17b are rigidly relied with each other.

In the rest position of the device 1, the activating means 15a, 15b is situated above, normally a small distance above, the upper (in FIGS. 2 and 4) face of the support plate 2. The upper face of each actuating means is flat and extends substantially in parallel to the support plate 2. In this rest position the distance between the female thread parts 17a, 17b is larger than the diameter of the screw actuator 4, so that the screw actuator 4 easily may be removed in this position and in a manner that will be described later on.

Each of the elastic springs 13a, 13b is slightly curved in a cross section and designed to bulge inwardly towards the symmetry axis of the holder means 6, when subjected to a force directed essentially perpendicular to the support plate 2. Thus, when the actuating means 15a, 15b are depressed towards the plate 2, the elastic springs 13a, 13b will deflect, so that the female thread parts 17a, 17b will be displaced inwardly towards each other. Also the actuating means 15a, 15b will move inwardly towards said axis due to the action of the springs 13a, 13b, when they are depressed towards the support plate 2. As best could be seen in FIG. 4, the radially outer edges of the actuating means 15a, 15b the elastic springs 13a, 13b and the oblique flanges 11a, 11b are designed in relation to each other, so that said edges of the actuating means will be guided by the inner walls of the oblique flanges 11a, 11b. Thus, when fully depressed (FIGS. 3 and 4) the upper faces of the actuating means 15a, 15b are flush with the support plate 2 and the outer edges bear against the inner walls of the oblique flanges 11a, 11b.

In this fully depressed position the parts 17a, 17b of the female thread are brought together to such an extent, that they form a portion of a female thread in accordance with the male thread of the screw actuator.

Figure 4:
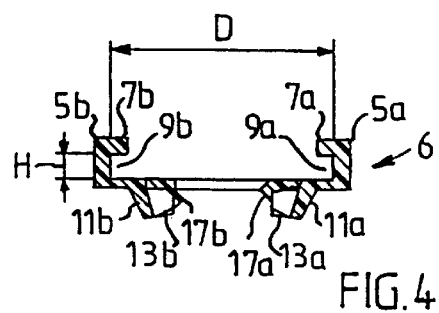
FIG. 4 is a sectional view of the closed device shown in FIG. 3 along the line IV—IV.

When to be used on an ampoule 23, the rim 25 of the ampoule having a thickness in correspondence with the height H of the flutes 9a, 9b, is inserted in the flutes 9a, 9b, thereby depressing the actuating means 15a, 15b to the closed position, shown in FIGS. 3 and 4. The screw actuator 24 may now be screwed into the opening 3 to be engaged with the female thread parts 17a, 17b.

Preferably the rim 25 of the ampoule 23 has an elliptic contour, the distance D of the device 1 then substantially corresponding to the long axis of the ellipse. The rim 25 of the ampoule 23 then is inserted with its long axis extending substantially in parallel with the flutes 9a, 9b. The holder means 6 and the ampoule 23 are then rotated about 90°, so that the rim 25 of the ampoule 23 will be clamped in the flutes 9a, 9b between the rims 5a, 5b and the support plate 2 in a bayonet-coupling-like manner. The device 1 may easily be released from the ampoule 23 by a corresponding relative rotation between the device 1 and the ampoule 23.

With reference to FIGS. 5–8 the function of the preferred embodiment will now be described.

A medical dual chamber ampoule 23, having a device 1 according to the invention mounted on its rim 25, includes a front chamber 24 for storing a sensitive medical component, e g a freeze-dried component, to be mixed with a solvent a short time before administration. The front end of said chamber includes a tip 27, having an outlet, which is sealed during storage and during the addition of the solvent. The rear end of the front chamber 24 is sealed by a resilient partition 29, e. g. of rubber, which is compressed between a constriction 31 provided in the ampoule 23 and the wall of the ampoule. The partition 29 is sized to allow flow into the front chamber 24 when not engaged with said constriction 31, but sealingly prevent flow thereto during storage.

The content in the front chamber 24 is such that it permits forward movement of the partition 29 for opening a flow communication from a rear chamber 33, situated behind the partition 29.

In the rear chamber 33 the liquid or solvent to be mixed with the freeze-dried medical component in the front chamber 24 is stored. The rear end of the chamber 33 is sealed by a seal or a plunger, e. g. of rubber, which is displaceable in sealing contact with the inner wall of the ampoule 23. Since the liquid essentially is non-compressible, a forward movement of the seal results in a corresponding movement of the partition 29.

When the liquid in the rear chamber 33 is to be added to the front chamber 24, the holder means 6 of the device 1 is mounted on the rim 25 of the ampoule 23 in the above-described manner. The screw actuator 4, having a relatively fine pitch, may then be inserted through the opening 3 of the holder means 6 and be rotated in engagement with the female thread 17a, 17b of the holder means 6. For accomplishing the rotational movement of the screw actuator 4, said member 4 is provided with an embossed finger grip 37. A further rotation of the screw actuator 4 will axially displace the seal 35 in the forward direction, leading to a forward movement of the partition 29. After a predetermined displacement of the partition 29 a communication is established between the chambers 24 and 33. A further rotation of the actuator 4 provides a smooth flow of liquid into the front chamber 24 due to the fine pitch of the threads. When the screw actuator 4 has been rotated in such a degree that the finger grip has reached the holder means 6, all liquid has been transferred to the front chamber 24, and in this position the seal 35 will rest against the partition 29. The mixing process is now completed and the prepared solution may be administered.

Figure 5:
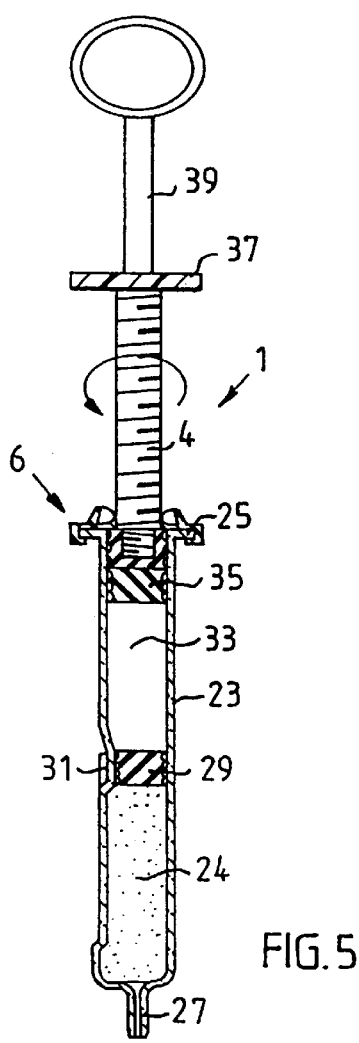
FIG. 5 is a sectional view of the device of the invention mounted on an ampoule, the screw actuator being in its initial position.
Figure 6:
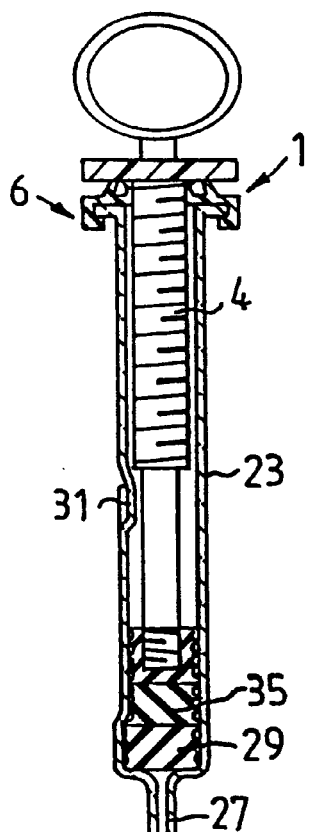
FIG. 6 is a sectional view of the device, similar to FIG. 5, the screw actuator being in its end position.
Figure 7:
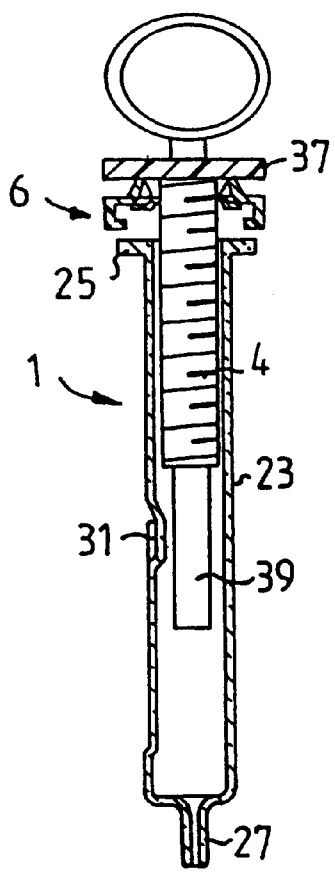
FIG. 7 is a sectional view similar to FIGS. 5 and 6, and showing the device released from the container or ampoule.

As can be seen in the FIGS. 5–7, the screw actuator 4 is hollow. In the bore of the actuator 4 a dispensing rod 39 is slidably received. When the actuator 4 has reached its bottom position, this dispensing rod 39 is used for expelling the solution in the chamber 24 through the tip 27 in desired amounts. This construction is known per se and forms no part of this invention.

Figure 8:
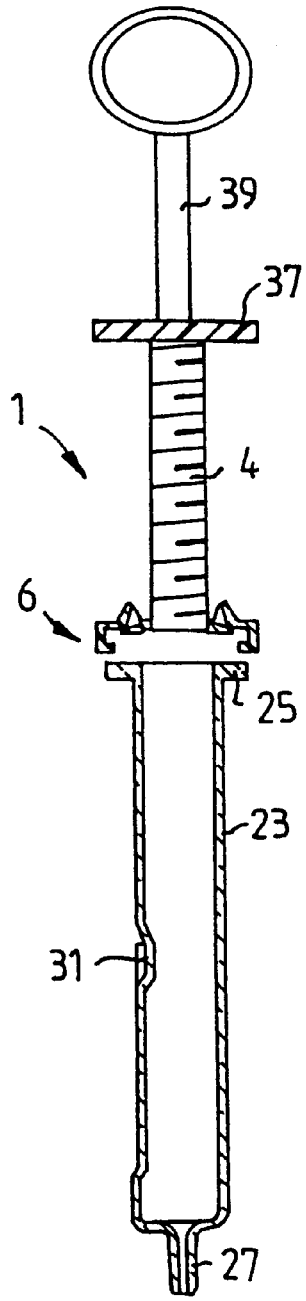
FIG. 8 is a sectional view similar to FIGS. 5–7 showing the device removed from the ampoule.

In FIG. 6, the final position is illustrated after the complete emptying of the ampoule 23 through the tip 27. Now the device 1 is to be reset to its starting position. In prior devices it was necessary to carry out a rotation of the actuator 4 all the way in opposite direction. The device 1 of the invention permits a quick and easy reset of the device to its initial position. The reset is accomplished by simply releasing the device 1 from the rim 25 of the container 23 by rotating it 90° about its axis and removing it from the ampoule 23, see FIG. 7. At the same time as the holder means 6 is disengaged from the rim 25, the actuating means 15a, 15b is released from its engagement with said rim 25, so that the female thread parts 17a, 17b of the holder means 6 loose its engagement with the screw actuator 4, which now may be taken out of the holder means 6 (FIG. 8). The device is now ready for a fresh ampoule 23. As is evident, some parts are excluded in the schematic view of FIGS. 7, 8 for the sake of simplicity.

It should especially be noted that the device of the invention may be used for various ampoules having different lengths.

It should further be obvious for a man skilled in the art that the device could be modified in many different ways. Thus, the female thread parts 17a, 17b need not automatically be actuated when the holder means is engaged with or disengaged from the container 23. Separate actuating means could be provided for accomplishing this function, which means may be actuated before or after the engagement of the device 1 with the container.

It should also be pointed out, that the holder means 6 could be designed in another way than a bayonet-like coupling. Any suitable coupling means may be employed for this purpose.

The preferred embodiment has been described with reference to a dual-chamber medical ampoule. However, it should be evident that any kind of container may be used, a single chamber ampoule as well as a multi-chamber ampoule. Likewise, instead of having a restriction for separating the chambers of the ampoule from each other during storage, the ampoule may comprise an overflow channel provided through a nip in the container wall, through which the solvent is transferred into the front chamber. In such a case a movable partition is provided behind said channel during storage, which during the liquid addition step will be displaced over said channel, thereby providing a communication into the front chamber.

The use of the device is not restricted to any particular kind of medicament or substance. It can be employed in all cases and in any field, wherein a smooth and undisturbed flow of an additive liquid is required.

What is claimed is:

1. A multi-chamber ampoule, comprising a container having at least one movable partition therein, the movable partition separating a first chamber from a second chamber and being adapted to sealingly isolate at least two substances to be mixed with each other;

a seal or plunger movably disposed in the container;

a holder connected to the container; and a screw actuator engageable with the seal or plunger for displacing the same in the container, the screw actuator having a male thread adapted to extend within the container as the screw actuator displaces the seal or plunger;

wherein the holder includes a female thread engaged or engageable with the screw actuator male thread; and wherein the screw actuator is provided with a bore therethrough for slidably receiving a dispensing rod.

2. The ampoule of claim 1, wherein an interior or exterior by-pass is provided in the container and is adapted to establish communication between the first chamber and the second chamber upon forward movement of the movable partition.

3. The ampoule of claim 2, wherein the by-pass comprises a constriction provided in the container.

4. The ampoule of claim 2, wherein the by-pass comprises a nip provided in the container.

5. The ampoule of claim 1, wherein the container comprises a dual-chamber ampoule.

6. The ampoule according to claim 1, wherein the ampoule is a medical multi-chamber ampoule.

7. The ampoule according to claim 1, wherein the holder comprises a substantially flat support plate having a central opening therethrough for the screw actuator and further wherein a pair of opposed flanges protrude perpendicularly from the support plate, the flanges and the support plate defining flutes for receiving a rim provided on the container.

8. The ampoule according to claim 7, wherein the flutes are adapted to clamp the rim of the container.

9. The ampoule according to claim 7, wherein the holder is releasably connectable to the container and further includes an actuator adapted for actuation when the holder is connected with the container, and wherein the actuator includes two plate-like members provided at a predetermined distance from the support plate in an open position of the holder, the plate-like members being adapted to be depressed by the container when the container is engaged with the holder and to cause the female thread to engage with the male thread.

10. The ampoule of claim 1, further comprising a dispensing rod slidably received in the bore of the screw actuator.

* * * * *

UNITED STATES PATENT AND TRADEMARK OFFICE
CERTIFICATE OF CORRECTION

PATENT NO. : 6,331,173 B1
DATED : December 18, 2001
INVENTOR(S) : Olle Ljungquist Page 1 of 1

It is certified that error appears in the above-identified patent and that said Letters Patent is hereby corrected as shown below:

<u>Column 6,</u>
Line 44, delete "and";
Line 46, replace "therethrough for slidably receiving a dispensing rod." with
-- therethrough; and wherein a dispensing rod is slidably received in the bore of the screw actuator. --
Beginning at line 60, replace "The ampoule according to claim 1," with -- A multi-chamber ampoule, comprising
      a container having at least one movable partition therein, the movable partition separating a first chamber from a second chamber and being adapted to sealingly isolate at least two substances to be mixed with each other;
      a seal or plunger movably disposed in the container;
      a holder connected to the container; and
      a screw actuator engageable with the seal or plunger for displacing the same in the container, the screw actuator having a male thread adapted to extend within the container as the screw actuator displaces the seal or plunger;
      wherein the holder includes a female thread engaged or engageable with the screw actuator male thread;
wherein the screw actuator is provided with a bore therethrough for slidably receiving a dispensing rod; and --.

Signed and Sealed this

Twenty-eighth Day of May, 2002

Attest:

*Attesting Officer*

JAMES E. ROGAN
*Director of the United States Patent and Trademark Office*